United States Patent [19]
Nadal

[11] Patent Number: 5,188,616
[45] Date of Patent: Feb. 23, 1993

[54] SYRINGE WITH DOUBLE PLUNGER

[75] Inventor: Guy Nadal, Poitiers, France

[73] Assignee: Celsa L.G. (Societe Anomyne), Chasseneuil Du Pointou, France

[21] Appl. No.: 777,660

[22] Filed: Oct. 16, 1991

[30] Foreign Application Priority Data

Oct. 23, 1990 [FR] France ................ 90 13105

[51] Int. Cl.$^5$ ................................. A61M 5/315
[52] U.S. Cl. .................... 604/218; 604/220; 606/200
[58] Field of Search ........... 606/200; 604/191, 193, 604/218, 220-221, 241, 189

[56] References Cited

U.S. PATENT DOCUMENTS

| | | | |
|---|---|---|---|
| 3,885,562 | 5/1975 | Lampkin | 604/189 |
| 4,256,132 | 3/1981 | Gunter | 137/14 |
| 4,317,446 | 3/1982 | Ambrosio et al. | 604/193 |
| 4,334,536 | 6/1982 | Pfleger | 604/193 |
| 4,735,616 | 4/1988 | Eibl et al. | 604/191 |
| 4,915,695 | 4/1990 | Koobs | 604/191 |
| 4,943,297 | 7/1990 | Saveliev et al. | 606/200 |

FOREIGN PATENT DOCUMENTS 1491768 10/1969 Fed. Rep. of Germany .
973467 2/1951 France .

Primary Examiner—John D. Yasko
Assistant Examiner—Corrine Maglione
Attorney, Agent, or Firm—Morrison Law Firm

[57] ABSTRACT

A single-syringe device capable of inserting its contents, such as a blood filter, into the body of a patient in either of two opposite directions exclusively chosen by an operator in a fail-safe manner. First and second plungers slide in opposite directions within the syringe, which is connected to a catheter or similar, to transfer the contents into the patient's body. The device is constructed so that only one plunger can be employed at a time. Each plunger and the end of the syringe it cooperates with is coded, by color or otherwise. Such a construction and coding insure fail-safe operation when the syringe's contents must be inserted in only one direction. For example, a blood filter that traps emboli must have the same orientation whether it be inserted in one direction from the patient's jugular vein or in the opposite direction from the patient's femoral vein.

10 Claims, 2 Drawing Sheets

SYRINGE WITH DOUBLE PLUNGER

BACKGROUND OF THE INVENTION

The invention relates to a syringe for introducing an article, such as, in particular, a vascular prosthesis, into the body of a recipient.

In the medical field, the use of syringes is of course widespread, these syringes comprising, as is known per se, a syringe element forming a cylinder for a plunger rod intended to move in this element so as to push the article which is contained therein in such a way as to introduce it at the appropriate site in the body of the recipient patient.

Such syringes are used in particular for the positioning of blood filters designed so as to be permeable to the flow of blood, while at the same time stopping clots capable of migrating towards the heart, in order to prevent, in particular, the risks of embolism.

The best known filters of this type are often in the form of a small truncated basket comprising a series of filiform legs. Examples of these can be found, in particular, in the Patent Applications FR-A-2 570 288 and FR-A-2 573 646, as well as in American Patent U.S. Pat. No. 3,952,747.

Such filters can be positioned via the jugular route or via the femoral route. However, in both cases, the filter must always be arranged with the same orientation in the receiving vein, as is illustrated in FIG. 1 where reference number 1 designates such a blood filter. The latter is in the form of a sort of basket having an essentially ogival head 3 from which there extend arms or legs 5 which are generally expandable and which are provided, if appropriate, with hooks 6 for anchoring to the wall of the vern. The legs 5 open outwards in such a way as to bear, via their free end 5a, against the wall of the vein 7 inside which the filter is essentially centered by being oriented in such a way that the blood flow (the direction of which has been shown diagrammatically by the arrow 9) first comes into contact with the legs and then the narrower joining head 3.

Also in this FIG. 1, the arrows 11 and 13 show, respectively, the direction of positioning of the filter via the femoral route (arrow 11) and via the jugular route (reference 13). It will be understood from this illustration that it is absolutely essential to orient the filter correctly when placing it in the positioning equipment (in this case the syringe) so that this filter can be delivered at the desired time by presenting first its head 3, if the femoral access route has been chosen, or its legs 5, if the jugular route.

There are at present two principal positioning techniques, with and without prepackaging of the prosthesis to be introduced.

In the first case, the practitioner orients the prosthesis manually at the time of its introduction into the positioning equipment. A human error is therefore always possible. Moreover, the prosthesis risks being damaged during its handling.

When the filter is prepackaged, it is thus contained in a syringe whose free end (opposite that end bearing the plunger rod) is designed to be connected to the positioning equipment, such as a catheter, through which the prosthesis will move as far as the site of the chosen blood vessel where it will then be released.

In this case, the surgeon must necessarily choose the method of access to the patient prior to the operation, and he cannot then change this method. However, the surgeon may be forced to reconsider his choice on account, in particular, of the tortuous nature of vessels or the like.

With this system, he can change from one access route to the other only by once again fitting on the endpiece of the catheter a new prepackaged assembly comprising a new complete syringe enclosing a new prosthesis placed in the direction corresponding to the access route now chosen. This therefore makes it necessary to have at one's disposal a double supply of prepackaged syringes. In addition, the loss of time involved in replacing a complete syringe with another one increases the operating risks.

Other solutions derived from the latter have also been proposed. However, the systems envisaged have proven difficult to implement in practice, particularly on account of the packaging requirements imposed by most prostheses, and especially by the percutaneous filters used most often.

OBJECTS AND SUMMARY OF THE INVENTION

The improved syringe proposed in the invention has the particular aim of overcoming the problems present encountered in the existing systems.

In short, the proposed solution consists in using a syringe element open at its two opposite ends and connected at one of the said ends to its actuation plunger, which will then be able to act from one side or the other on the prepackaged article to be injected, and this according to the direction of introduction selected.

More precisely, the syringe of the invention is characterised in that the syringe element has two open ends through which the article to be introduced can pass, such as, for example, the vascular prosthesis chosen, each of the ends of this syringe element being equipped with a connection means capable of cooperating with a complementary connection means fitted on the plunger and through which the rod of the latter can slide, from one or other of the ends of the syringe element.

A specific syringe element will preferably be assigned two types of plunger whose means of connection to this element will be designed differently from one another, both of them being, despite this, compatible with the complementary connection means situated at one or other of the ends of the syringe element.

And according to a complementary characteristic of the invention, the complementary "foolproof" connection means of the plunger and of this syringe element will advantageously be separable from one another.

By virtue of the characteristics of the invention, the practitioner will therefore be able to react very quickly if it is found that the access route chosen is unsuitable, since he has at his disposal means that allow him to change access route without any risk.

In order to avoid any risk of confusion regarding the direction of introduction of the packaged article, different safety means can be envisaged, ensuring, for example, that a given type of plunger can cooperate only with one of the ends of the syringe element. In the same way, it will be advisable to design differently the two connection means provided at the two opposite ends of the syringe element, it also being possible for this element to have, alongside the connection means in question, a profile or a shape specific to each end.

It has also been envisaged that the syringe may comprise external, visual indicator elements comprising a color code common to one part of a given plunger and to a suitable site on the body of the corresponding syringe, in such a way as to prompt the user to put the chosen plunger into position from a given side of the body of this syringe.

It will of course be understood from reading the previous description that, within the context of the invention, it has been necessary to develop a compatible connection system between the plunger and the syringe element. For this, a plunger has been devised, which is intended in particular for a syringe of the type mentioned hereinabove and which is characterised in particular in that it comprises a rod which can slide inside a ring bearing a connection means capable of cooperating in a removable manner with a complementary connection means formed at an open end of an associated syringe element.

It will also be noted that, in addition to the syringe and its plunger, the invention also relates to the specific application of this syringe for the introduction of a vascular prosthesis into the body of a recipient patient, the connection means of the body of this syringe preferably also forming, within the scope of this application, a compatible means for removably connecting to a complementary connection means formed on the catheter for introduction of the prosthesis.

Other characteristics and advantages of the invention will emerge from the description which follows and in which reference is made to the attached drawings, in which:

BRIEF DESCRIPTION OF THE DRAWINGS in addition to FIG. 1, which has already been discussed and which illustrates an example of a blood filter in position in a venous pathway, FIGS. 2 and 3 show, in a longitudinal cutaway view, one and the same syringe element provided at one or other of its ends with a suitable plunger, FIGS. 4 and 5 show, in partial cross-section and in isolation, the plungers used on the body of the syringe in FIGS. 2 and 3, respectively, FIGS. 6 and 7 show, in an external view from the side, in the direction of the arrows VI and VII in FIGS. 2 and 3, the syringe element on its own, bearing visual identification elements making it possible to establish the intended direction of introduction of the article or element contained in the body of this syringe, and FIG. 8 illustrates, in a perspective view, an alternative embodiment of the syringe of the invention.

DETAILED DESCRIPTION OF THE PREFERRED EMBODIMENT

Figure 1:
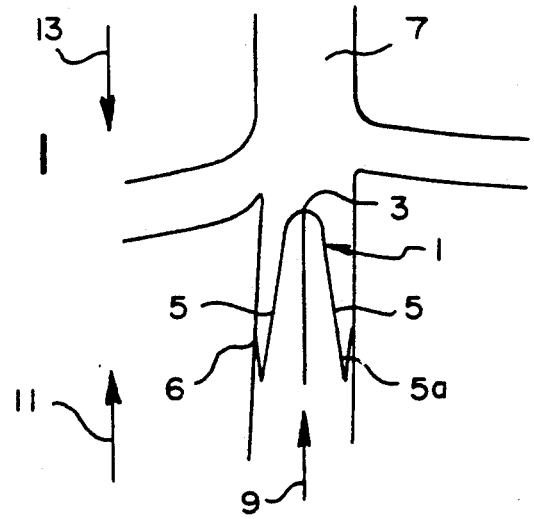
Figure 2:
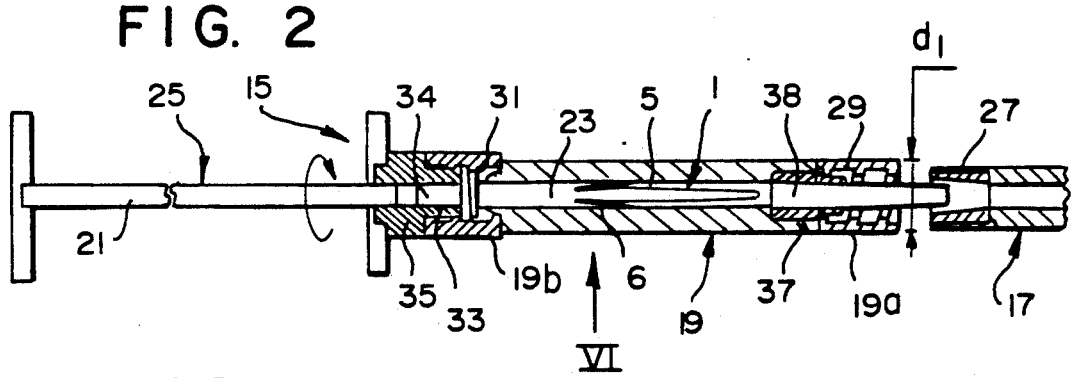
Figure 3:
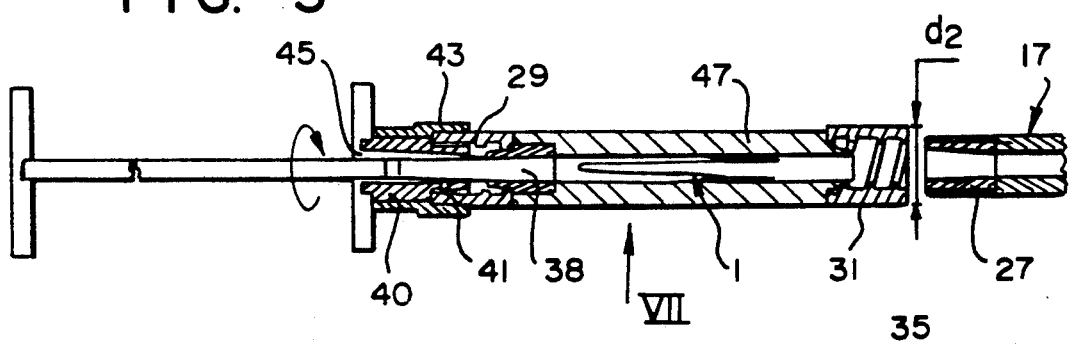

Referring first of all to FIGS. 2 and 3, these show a syringe intended in this case to ensure the introduction, via a catheter 17, of the prosthesis 1 which, at this moment, is in place inside the syringe element 19. This element is in the form of a tubular piece open at its two opposite ends 19a, 19b so as to permit the engagement (in the syringe) or the removal (particularly towards the catheter 17) of the prosthesis 1. These openings are also designed to permit the assembly of a plunger, whose activation rod, designated by 21, is of course designed to penetrate inside the passage 23 of the syringe element in which the prosthesis is in this case packaged.

At its first open end 19a, the syringe element is equipped with a first connection means consisting in this case of a tapped endpiece 29 designed to cooperate in a removable manner with the threads of a complementary endpiece 27 provided on the catheter 17. At its opposite end 19b, this same syringe element comprises another endpiece (or ring) likewise equipped with a connection means also consisting in this case of a tapped part or ring 31 inside which there are here removably engaged the complementary connection threads 33 of the ring 35 which, with the rod 21, constitute the plunger 25. Of course, the inner passage 34 reserved for the rod in the middle of the ring, has been designed so that the passages 34 and 23 can coincide and provide the rod 21 with the best translational guidance.

So, means 29, 33 are fail safe means for avoiding the connection of the non-appropriate plunger to the syringe 19.

To the extent that, in the example illustrated, the syringe chosen is intended to ensure in particular the introduction of a percutaneous blood filter provided with hooks 6 which risk clinging to the wall of the endpiece 27 of the catheter, it will be noted that the end towards the right in FIG. 2 (and towards the left in FIG. 3) of the syringe element is provided with a fine complementary endpiece 37 which is externally truncated and is passed through from one end to the other by a channel 38 of the same diameter as the passage 23, in whose continuation the channel is formed. The shape and the length of the endpiece 37 have been designed in this case so that it passes through the tapped part 29 and can open out into the catheter 17, thus allowing the hooks 6 of the filter to pass without hindrance beyond the often critical point of the endpiece 27, its tapered shape moreover ensuring that it does not in any way obstruct the connection between the catheter and the associated connection means of the syringe element.

Indeed, in the present case, it will also be possible for this endpiece 37 to serve as a means for indicating the direction of introduction of the filter, since it is provided at only one of the ends of the syringe element.

However, this endpiece will preferably have only a complementary indicating role, the safety associated with the direction of movement of the filter preferably being ensured essentially by the presence of two different plungers, or more exactly of two different plunger rings each provided with specific connection means which can be adapted solely to one or other of the two connection endpieces 29, 31 of the syringe element.

This is also clearly illustrated by a comparison of FIGS. 2 and 3, FIG. 3 showing a plunger ring 40 which differs from that in FIG. 2 insofar as, at its threaded part 41 which is designed to cooperate via the inside with the tapping 29 of the same syringe element 19, there is associated an external annular part 43 locally surrounding the endpiece 29. Giving the endpieces 29 and 31, for example, different profiles or external diameters $d_1$ and $d_2$ will thus prevent the assembly ring 40 from cooperating with the "unauthorised" endpiece 31 of the syringe element. In addition, with such a structure, it will be possible to retain for both ends 29 and 31 an identical tapping, thus permitting the use of the same catheter 17, so that its endpiece 27 comes into connection with one or other of the ends of the syringe element for an engagement of the filter in one direction or the other.

However, it would have been possible, of course, in an alternative, to provide endpieces 29 and 31 equipped with connection means differing from one another (each of these means nevertheless remaining compatible with one or the other of the assembly rings of the plunger).

Still in FIG. 3, it will moreover be noted that the assembly ring 40 here has an internal passage 45 which is slightly wider than that permitting a tight guiding of the rod 21 of the plunger, so way that this rod is essentially guided from the inlet of the syringe element by the wall of the channel 38 of the fitting 37.

To complete the description of the syringe element, it will also be noted, and this is shown more clearly in FIG. 3, that it will be possible for this element to be made, for example, in such a way that its connection endpieces 29, 31 are connected to each other via an intermediate tubular part 47 ending, at the side opposite the fitting 37, just at the inlet of the endpiece 31, no extension being necessary here since, in this configuration, the filter should emerge from the syringe legs first.

Figure 4:
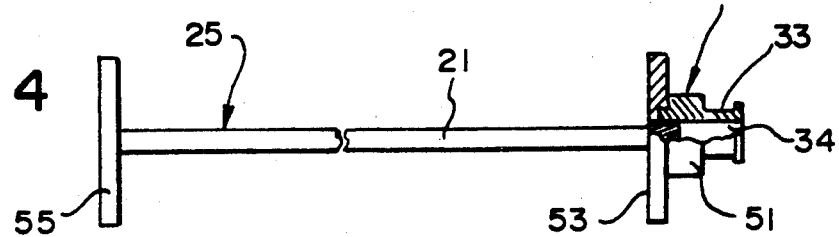
Figure 5:
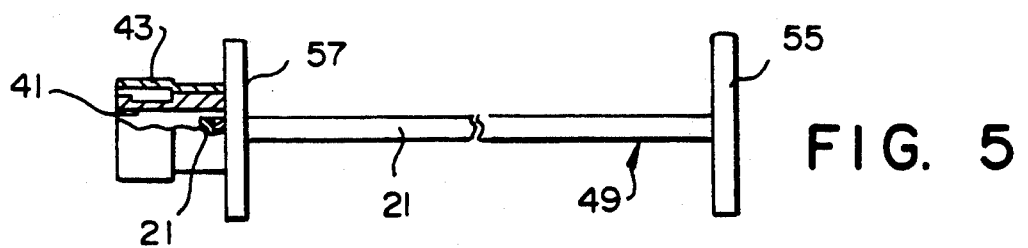

Let us now refer to FIGS. 4 and 5, in which the two types of plungers, which have been favored a priori, are illustrated on their own.

In the context of the use of the concept of the invention, it has been decided arbitrarily that the plunger designated by 25 in FIG. 4 (and which is shown in FIG. 2) be used when it is desired to introduce the filter via the femoral route, that is to say when the syringe is to be prepared as illustrated in FIG. 2.

Still in FIG. 4, the shape of the ring 35 will be noted, which ring bears the connection means of the plunger and through the passage 34 of which ring the rod 21 can of course slide. Behind its threaded part 33, the ring 35 has an external shoulder 51 forming a stop, then a bearing flange 53, while the rod 21, at the end opposite that via which it engages through the passage 34 of the ring, finishes in an enlarged part forming a pusher 55.

Referring now to the other plunger in FIG. 5, it will be noted that it also has, behind its threaded inner part 41 which is surrounded by the annular profile 43, a bearing flange 57, it being possible for the same rod 21 with its pusher 55 to be used for each of the plungers.

To complete the identification of the correct orientation of the syringe, it has been envisaged to provide it with external visual indicator elements which can comprise a color code common to one part of the plunger and of the syringe element.

Figure 6:
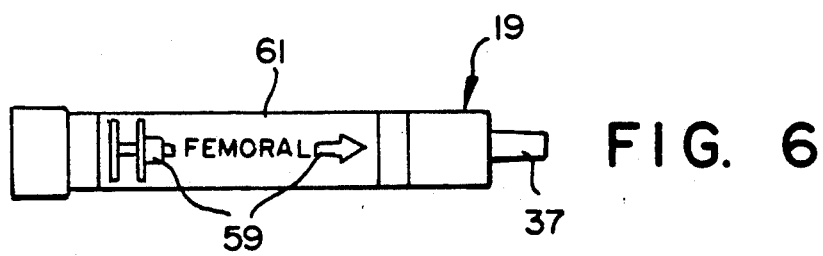
Figure 7:
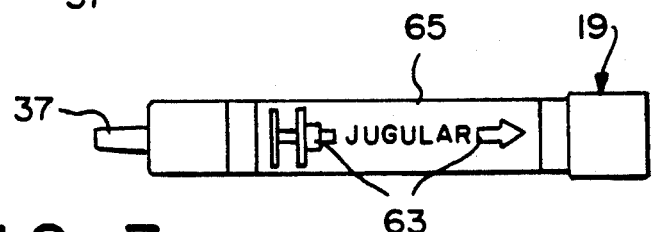

In this respect, it will be possible, for example, to envisage forming the flange and the pusher 55 of the plunger 25 (intended in the chosen example for introduction via the femoral route) in a blue color, while a red color can be given to the same pieces 55 and 57 of the plunger 49 (chosen in this example for introduction via the jugular route). As regards the syringe element, it can comprise, for example, on one side (see FIG. 6) signs 59 and a wording 61 indicating, for example, for the femoral access route, the end where the plunger should be fitted and the end through which the filter should emerge, while on the opposite side (see FIG. 7) this same element can have, on the outside, marks 63 and 65 indicating the same signs reversed for introduction via the jugular route. Moreover, the same colors as those used for the plungers can be used for the wordings shown on one side or the other of the syringe element, depending on which of the access routes has been chosen.

Although the principle of a removable connection between the plunger and syringe element of the male-/female thread type may be preferred, it would of course be possible to envisage other types of mechanical connection capable of preventing the risks of errors as regards the direction of introduction of the filter, such as, for example, the connections of the, bayonet type or with associated square, hexagonal etc., geometrical shapes.

Figure 8:
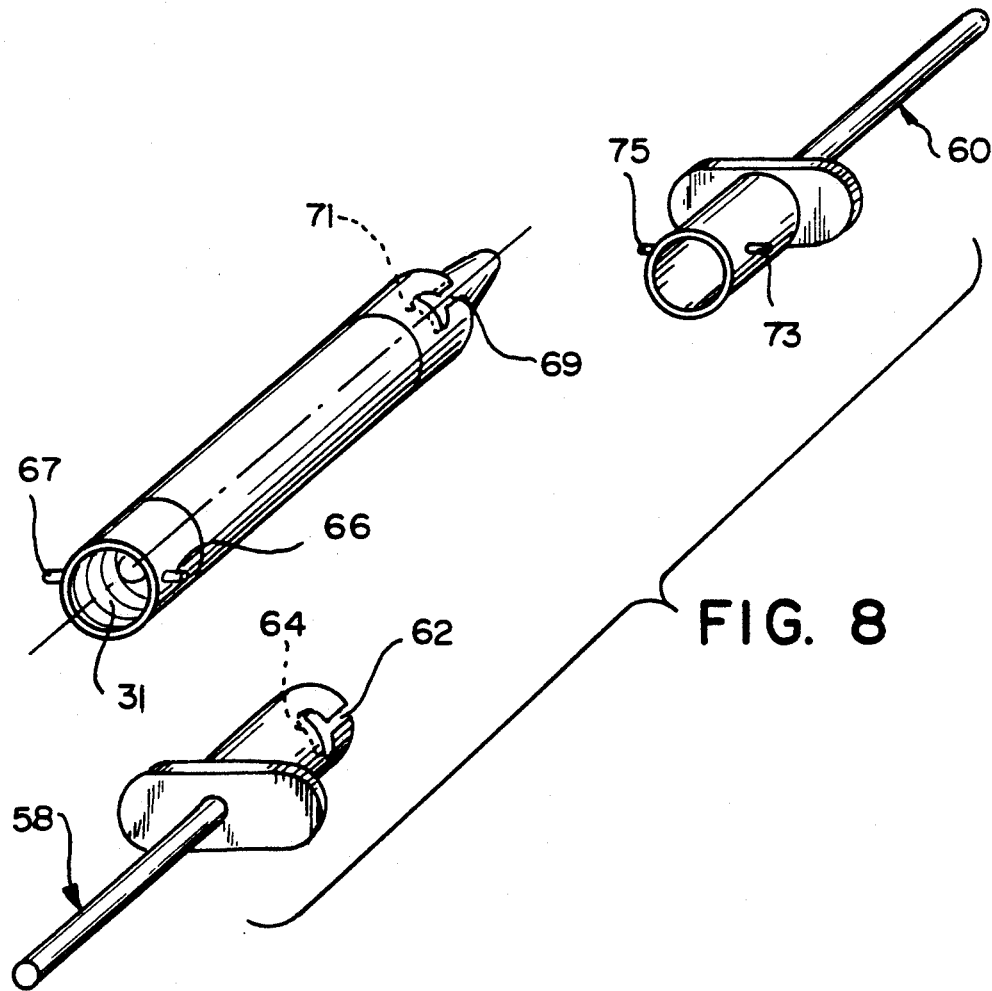

FIG. 8 shows, by way of example, an alternative embodiment of the syringe with a bayonet-type connection between the plunger and syringe element.

In this example, the connection ring of the first plunger designated 58 is equipped with two T-shaped slots 62, 64 designed to cooperate with two pins 66, 67 provided in a complementary fashion at one of the ends of the associated syringe element, this element itself having at its opposite end two diametrically opposite T-shaped slots 69, 71 designed to receive the two associated pins 73, 75 provided, in a complementary fashion of course, on the hollow endpiece or ring of the other plunger 60.

It is clear that such a method of connection does not in any way prohibit the syringe element from having on the inside, at its ends, the same tappings (such as 31) intended to ensure the connection with the complementary introduction catheter 17, and in so doing retaining the advantages afforded by the syringes in FIGS. 2 and 3.

In a possible complementary application, it will be noted that, in an alternative embodiment, it could be possible to make the endpieces 29, 31 of the syringe element integral with the corresponding pierced rings 40, 35 of the plungers (only the plunger rods then being removable), even if this means providing, for example, a tapping at the outer end of these rings in order to permit, if necessary, a connection to a catheter of the type, for example, designated 17 in FIG. 2.

Of course, although the preceding description has been made essentially with reference to a syringe intended for the introduction of a blood filter, it would be possible to use this syringe (by adapting its dimensions and in particular those of the orifices and passages) for injecting other articles, such as other types of prosthesis, or even liquids.

I claim:

1. A syringe comprising:
    a tubular syringe body having a first and a second opened end;
    said first and said second opened end being opposite one another;
    a first plunger insertable into said first end of said syringe body and slidable therethrough;
    a second plunger insertable into said second end of said syringe body and slidable therethrough; and
    fail-safe safety means provided on said first and said second plungers and on said syringe body for allowing exclusively a one of:
    the insertion of said first plunger into said first end of said syringe body; and
    the insertion of said second plunger into said second end of said syringe body.

2. A device for introducing contents of a syringe into a patient, comprising:
    a tubular syringe body having a first and a second opposite opened ends around which are disposed respectively first and second connecting means;
    a first plunger unit comprising:
        a first plunger rod adapted for sliding in said syringe body; and
        a first ring through which said first plunger rod is slidable;
    said first ring being provided with third connecting means removably connectable to said first connecting means of said syringe body;

a second plunger unit comprising:
  a second plunger rod adapted for sliding in said syringe body; and
  a second ring through which said second plunger rod is slidable;
said second ring being provided with fourth connecting means removably connectable to said second connecting means of said syringe body;
hollow introducing means having a first open end around which are disposed fifth connecting means removably connectable to a one of said first and second connecting means of said syringe body in the absence of a one of the first and the second plunger unit; and
said introducing means being effective for introducing into said patient the content of said syringe body.

3. A device according to claim 2 wherein:
said first, second, third and fourth connecting means are provided with fail-safe safety means for avoiding the removable connection therebetween of said first and fourth connecting means, and said second and third connecting means, respectively.

4. A device according to claim 3 wherein said first, second, third, fourth, and fourth removable connecting means comprise screwing means.

5. A device according to claim 2 wherein said syringe body comprises:
at each of said first and said second ends thereof, an annular endpiece provided with said first and said second connecting means, respectively; and
near said first or said second end thereof, a truncated tubular part passing through a said endpiece for forming a fail-safe safety means, thereby avoiding the connection therebetween of said first and fourth connecting means, and said second and third connecting means, respectively.

6. A device according to claim 2 wherein:
said first connecting means comprises internal female screwing means and external male bayonet means;
said second connecting means comprises internal female screwing means and external male bayonet means;
said third connecting means comprises female bayonet means removably connectable to said external male bayonet means of said first connecting means;
said fourth connecting means comprises external male bayonet means removably connectable to said female bayonet means of said second connecting means; and
said fifth connecting means comprises external male screwing means screwable into said female screwing means of a one of said first and said second connecting means.

7. A device according to claim 2 wherein said first and second plunger units and said syringe body are each eternally provided with visual indicating means for indicating the end of said syringe body to which a one of said first and said second plunger units is to be connected.

8. A device according to claim 2 wherein:
said first plunger unit is at least partially of a first color;
said second plunger unit is at least partially of a second color; and
said syringe body is at least partially of said first color at said first end thereof and of said second color at said second end thereof.

9. A device according to claim 2 wherein:
said first and said third connecting means are adapted for cooperating in connection by partial overlapping of said first end of said syringe body by a portion of said first ring; and
said second and said fourth connecting means are adapted for cooperating in connection by partial overlapping of said fourth connecting means of said second ring with said second end of said syringe body.

10. A device according to claim 2 wherein said contents of said syringe body is a vascular prosthesis and said hollow introducing means is a catheter for introducing said vascular prosthesis from said syringe body into a blood vessel of a patient.

* * * * *